(12) United States Patent
Tseng

(10) Patent No.: US 9,964,485 B2
(45) Date of Patent: May 8, 2018

(54) OPTICAL DEVICE AND METHOD FOR DETERMINING AN OPTICAL PROPERTY OF SPECIMEN

(71) Applicant: NATIONAL CHENG KUNG UNIVERSITY, Tainan (TW)

(72) Inventor: Sheng-Hao Tseng, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 162 days.

(21) Appl. No.: 14/844,536

(22) Filed: Sep. 3, 2015

(65) Prior Publication Data
US 2017/0067823 A1    Mar. 9, 2017

(51) Int. Cl.
*G01N 21/00* (2006.01)
*G02B 6/00* (2006.01)
*G01N 21/47* (2006.01)
*G01N 21/31* (2006.01)
*A61B 5/00* (2006.01)

(52) U.S. Cl.
CPC ....... *G01N 21/4738* (2013.01); *A61B 5/0059* (2013.01); *G01N 21/31* (2013.01); *G01N 21/4795* (2013.01)

(58) Field of Classification Search
CPC . G01N 21/31; G01N 21/4738; G01N 21/4795

USPC .............................................. 356/432; 385/12
See application file for complete search history.

(56) References Cited

U.S. PATENT DOCUMENTS

| | | | | |
|---|---|---|---|---|
| 5,917,190 A * | 6/1999 | Yodh | ........ | G01N 21/4795 250/458.1 |
| 2005/0226548 A1* | 10/2005 | Durkin | ........ | G01N 21/31 385/12 |
| 2010/0160754 A1* | 6/2010 | Durkin | ........ | A61B 5/0075 600/342 |
| 2011/0263955 A1* | 10/2011 | Narita | ........ | A61B 1/00165 600/341 |

* cited by examiner

*Primary Examiner* — Sunghee Y Gray
(74) *Attorney, Agent, or Firm* — Huffman Law Group, PC

(57) ABSTRACT

A diffuse reflectance spectroscopy system for determining an optical property of a specimen and a method for operating the same are provided. The system includes: a light emitting unit comprising a light emitting terminal, the light emitting unit configured to emit steady light; an optical medium arranged at one end of the device, the optical medium being controllable to switch between multiple optical states and configured to deliver the steady light to the specimen through the optical medium in different optical states, wherein the optical medium comprises a first surface in contact with the light emitting terminal of the light emitting unit and a second surface for contact with the specimen; and a detecting module comprising one or more receiving terminals for receiving light scattered from the specimen for determining the optical property of the specimen.

11 Claims, 4 Drawing Sheets

(a)

(b)

(c)

OPTICAL DEVICE AND METHOD FOR DETERMINING AN OPTICAL PROPERTY OF SPECIMEN

FIELD

The present disclosure generally relates to optical spectroscopy, and more specifically to methods and systems for measuring optical properties of a specimen with diffuse reflectance spectroscopy.

BACKGROUND

Diffuse reflectance spectroscopy (DRS) has been widely used as a non-invasive tool for obtaining quantitative information about the optical properties of in-vivo tissue (e.g., absorption and scattering properties of biological molecules in tissue). In a DRS system, a light beam is directed into a target specimen (such as a biological tissue) and scattered within the specimen. Light diffusely reflected from within the specimen is then captured to obtain a reflectance spectrum thereof. The reflectance spectrum is then combined with light propagation models to determine the optical properties (e.g., absorption and scattering properties) of the specimen. The acquired optical properties can then be related to the composition, structure and microstructure of the specimen.

As shown in FIG. 1, a DRS system may use one of the following light sources: (1) a steady light source: emitting a light with constant intensity into the specimen, shown in FIG. 1(a); (2) a pulsed light source: emitting a modulated time domain light into the specimen, shown in FIGS. 1(b); and (3) a modulated frequency light source: emitting a light with modulated sine wave frequency into the specimen, shown in FIG. 1(c).

FIG. 2 shows a conventional DRS system 200 with multiple source-detector separations. The DRS system 200 comprises a light emitting unit 201 and two light detecting units 202a and 202b. The light emitting unit 201 and the two light detecting units 202a and 202b are placed on adjacent spots of a surface of a specimen 203. The light emitting unit 201 and the light detecting unit 202a are separated by a distance D1 while the light emitting unit 201 and the light detecting unit 202b are separated by a distance D2 (which is greater than D1). Since the source-detector separations D1 and D2 are different, the reflectance spectrum measured at light detecting unit 202a will be different from the reflectance spectrum measured at light detecting unit 202b, as a distinction can be made between light that has traveled shorter distances through the target specimen (low penetration, less interaction with the target specimen) and light that has propagated through the target specimen for longer times and distances (penetrated deeper, more interaction with the target specimen). Therefore, the two reflectance spectra can be analyzed and combined to obtain sufficient information for the separation of the scattering and absorbance properties/coefficients.

Nevertheless, a conventional DRS system with multiple source-detector separations has the following drawbacks. Firstly, the source-detector separation must be large enough for accurate measurement. This makes it extremely difficult to reduce the size of the DRS system. Also, having multiple source-detector separations means that some source-detector separations are larger than other source-detector separations, and larger source-detector separation implies that, when taking measurements, light diffusely reflected from deeper (underlying) layers of a target specimen cannot be avoided. That is, the light received at shorter distances (D1) only contains information on the shallow layer, while at longer distances (D2) the collected light is influenced by the shallow layer as well as the underlying layers. Therefore, it is not practical to use a DRS system with multiple source-detector separations to determine the optical properties of the shallow layers of a target specimen. Moreover, for a DRS system with multiple source-detector separations, due to inhomogeneity in optical properties within the target specimen, diffuse reflectance taken by different detectors cannot be easily calibrated for the system response using homogeneous reference tissue simulating phantom with known optical properties. Furthermore, the conventional DRS system 200 needs at least three optical fibers: one for the light emitting unit 201 and at least two for the light detecting units 202a and 202b. Moreover, an optical switch (not shown) is required for the conventional DRS system 200 to switch between the light detecting units 202a and 202b. Therefore, a novel DRS system is still needed to overcome the aforementioned drawbacks.

SUMMARY OF INVENTION

The present invention provides an economical, accurate and effective device and method for determining an optical property of a specimen.

In one embodiment, the present invention provides an optical device for determining an optical property of a specimen, comprising a light emitting unit comprising a light emitting terminal, the light emitting unit configured to emit light; an optical medium arranged at one end of the device, the optical medium being controllable to switch between multiple optical states and configured to deliver the steady light to the specimen through the optical medium in different optical states, wherein the optical medium comprises a first surface in contact with the light emitting terminal of the light emitting unit and a second surface for contact with the specimen; and a detecting module comprising one or more receiving terminals for receiving light scattered from the specimen for determining the optical property of the specimen.

In another embodiment, the subject invention provides a method for determining an optical property of a specimen, comprising providing light; switching an optical medium in between different optical states; directing the steady light through the optical medium into the specimen in the different optical states of the optical medium; scattering the steady light in the specimen; and receiving the light scattered from the specimen for determining the optical property of the specimen.

BRIEF DESCRIPTION OF THE DRAWINGS

Aspects of the present disclosure are best understood from the following detailed description when read with the accompanying figures. It is noted that, in accordance with standard industry practices, various features are not drawn to scale. In fact, the dimensions of the various features may be arbitrarily increased or reduced for clarity of discussion.

DETAILED DESCRIPTION

Figure 1:
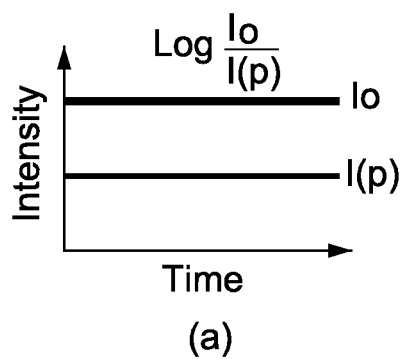
FIG. 1 shows different light sources used in a DRS system.
Figure 1:
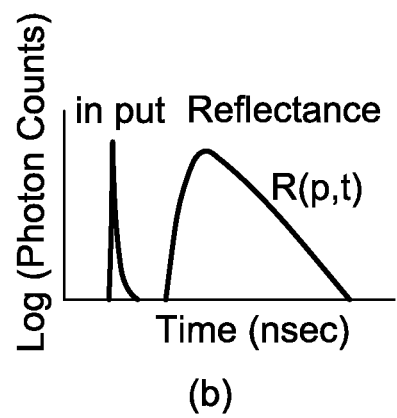
Figure 1:
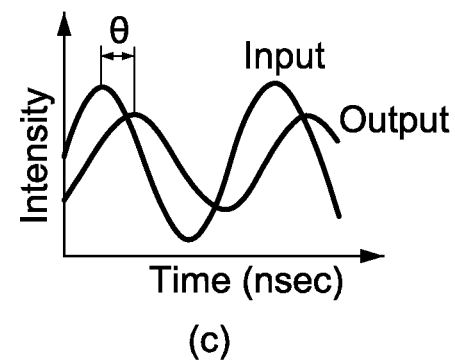
Figure 2:
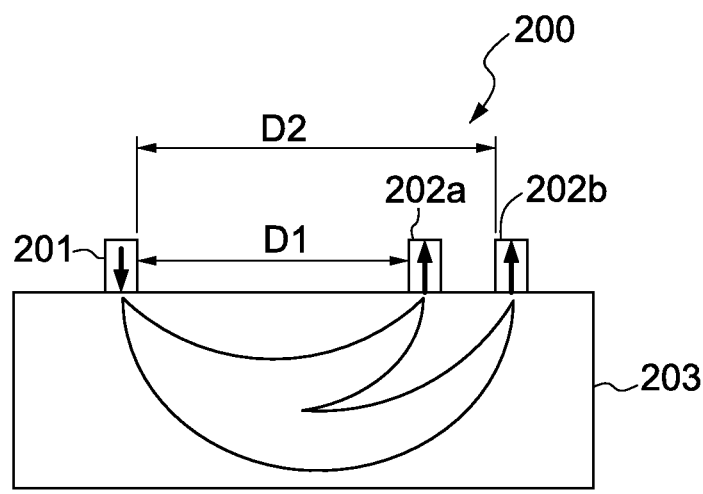
FIG. 2 shows a conventional DRS system with multiple source-detector separations.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. Additionally, the present disclosure may repeat reference numerals and/or letters in the various examples. This repetition is for the purpose of simplicity and clarity, and does not in itself dictate a relationship between the various embodiments and/or configurations discussed.

Furthermore, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations), and the spatially relative descriptors used herein may likewise be interpreted accordingly.

The production and implementation of the embodiments are discussed in detail below. It should be understood, however, that the present invention provides many applicable inventive concepts that can be embodied in a wide variety of specific contexts. The specific embodiments discussed are merely illustrative of specific ways to produce and implement the invention, and do not limit the scope of the invention.

Figure 3:
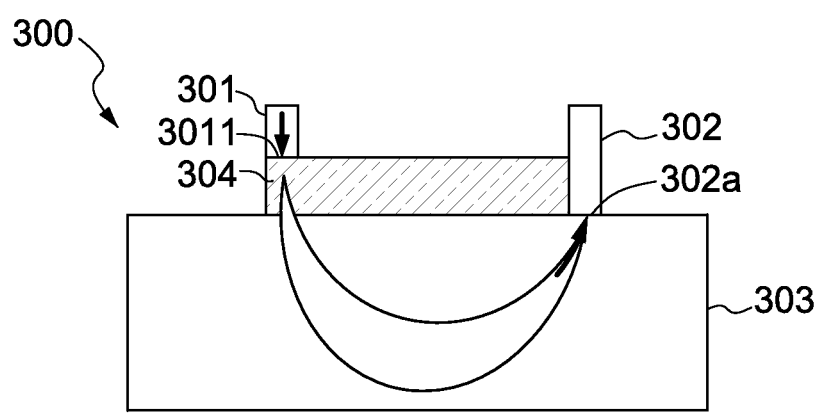
FIG. 3 is a schematic diagram illustrating a DRS device in accordance with one embodiment of the present disclosure.

FIG. 3 is a schematic diagram illustrating an optical device 300 in accordance with one embodiment of the present disclosure. Referring to FIG. 3, the optical device 300 (such as a DRS device) comprises a light emitting unit 301, a detecting module 302 and an optical medium 304. The light emitting unit 301 comprises a light emitting terminal 3011, and the light emitting unit 301 is configured to emit light. In one embodiment, the light emitted by the light emitting unit 301 is steady-state white light (i.e., a combination of lights of different wavelengths). The optical medium 304 has a first surface in contact with the light emitting terminal 3011 and a second surface opposing to the first surface. The second surface of the optical medium 304 is in contact with a specimen 303 in operation. The detecting module 302 comprises at least one receiving terminal 302a. Note that the arrows (below the light emitting terminal 3011 and receiving terminal 302a) indicate the directions in which the beam of light travels. That is, light emitted by the light emitting unit 301 first enters and meanwhile is scattered by the optical medium 304. The optical medium 304 is controllable to switch between multiple optical states. Due to the differences in optical properties between the different optical states with different scattering and absorbance properties/coefficients of the optical medium 304, the light passing through the optical medium 304 in different states would result in different propagation properties. The optical medium 304 delivers the light to the specimen 303 in different optical states. Then, the specimen 303 scatters the light, and then the receiving terminal 302a receives the light scattered from the specimen 303. In one embodiment, the receiving terminal 302a comprises a photo sensor.

The received light can be used to determine the optical property of the specimen 303. In one embodiment, the determined optical property comprises at least one of the following: an absorption coefficient and a scattering coefficient.

In one embodiment, the received light is passed to a spectrometer (not shown) coupled to the detecting module 302, wherein the spectrometer analyzes the reflectance spectrum of the received light.

According to the present invention, the receiving terminal 302a receives the light diffusely reflected from within the specimen 303 for each optical state of the optical medium 304. For example, light passing through the optical medium 304 in its first optical state would be introduced into the specimen 303 with a first set of propagation parameters. This light beam is scattered in the specimen 303. The receiving terminal 302a is configured to receive light diffusely reflected from within the specimen 303 to obtain a first reflectance spectrum of the specimen 303 associated with the first optical state of the optical medium 304. Similarly, the detecting module 302 would obtain a second reflectance spectrum of the specimen 303 associated with the second optical state of the optical medium 304. The first and second reflectance spectra can be analyzed to obtain sufficient information for determining desired optical properties of the target specimen 303. Unlike the conventional DRS system 200 (which needs at least three optical fibers; one for the light emitting unit 201 and at least two for the light detecting units 202a and 202b), the optical device 300 of the present invention may only need two optical fibers for each of the light emitting unit 301 and the detecting module 302. Furthermore, an optical switch is not required for the optical device 300.

In one embodiment, the optical property of the specimen 303 is calculated from the light received at the receiving terminal 302a through a photon transport model. For example, the scattering and absorbance properties/coefficients of the optical medium 304 may be separately estimated by fitting the measured reflectance spectra to a photon transport model such as Monte Carlo algorithm and/or a diffusion algorithm. Monte Carlo simulation is a method for calculating the scattering and absorption properties/coefficients of a specimen from diffuse reflectance measurements in an iterative process that repeatedly models reflectance values from a set of estimated specimen optical parameters and calculates the error between the measured diffuse reflectance and the modeled reflectance values, and calculating the scattering and absorption characteristics of the specimen from the estimated specimen optical parameters that result in a minimum error.

Additionally, the measured first and second reflectance spectra (that are respectively associated with the first and second optical states of the optical medium 304) can be used for quick calibration of system repose errors. For example, the first spectrum may be normalized with respect to the second spectrum to yield normalized reflectance spectra that can effectively correct or compensate for a number of factors, such as lamp intensity fluctuations, wavelengthdependent instrument response, inter-device variations, and fiber bending losses that occur while a measurement is taken.

In one embodiment, the optical medium 304 has more than two optical states. For example, the optical medium 304 may have five optical states and the detecting module 302 is configured to obtain five reflectance spectra associated with each of the five optical states of the optical medium 304. Similarly, one of the obtained five reflectance spectra may be selected as the reference reflectance spectrum and the rest of the reflectance spectra may be normalized with respect to the reference spectrum to yield normalized reflectance spectra for accurate derivation of optical properties of the target specimen 303. In view of the above, there is no need for the DRS device 300 to use any reference phantom with known optical properties for calibration of any system response.

In one embodiment, the optical medium 304 may be a thermally sensitive material. A controller may be a thermal controller that can change the thermal condition (e.g., temperature) of the optical medium 304. Therefore, switching among different optical states can be easily carried out by changing the thermal condition of the optical medium 304 (e.g., by heating it up or cooling it down). For example, the optical medium 304 may be heated up to remain in a first temperature (e.g., 40 degree Celsius), which results in a first optical state of the optical medium 304. While the optical medium 304 may have a second temperature different from the first temperature (e.g., 60 degree Celsius) and a second optical state. In one embodiment, the optical medium 304 may be controlled to have a temperature ranging from about 5 degree Celsius to about 80 degree Celsius.

In one embodiment, the optical medium 304 is a turbid medium, wherein the turbid medium may comprise a liquid crystal. The multiple optical states of the turbid medium depend on voltages applied to the turbid medium. In one embodiment, the optical medium 304 is coupled to and controlled by a controller (not shown) for providing different voltages so as to switch among different optical states.

The controller coupled to the optical medium 304 may be an AC or DC power supply that is configured to provide electric signals of different magnitudes to the optical medium 304. The power supply may be configured to provide different voltages to the optical medium 304. In response to each of the different voltages applied, the optical medium 304 may be configured to exhibit a unique optical state. For example, a first voltage (e.g., 150 V) may be applied to the optical medium 304 so as to switch the optical medium 304 into a first optical state, and a second voltage (e.g., 200 V) may be applied to the optical medium 304 so as to switch the optical medium 304 into a second optical state. In one embodiment, the voltage applied to the optical medium 304 may range between about 0 V to about 400 V. Preferably, the voltage applied to the optical medium 304 may range between about 100 V to about 400 V. It should be noted that the optical medium 304 may have more than two optical states. For example, the optical medium 304 may have five optical states corresponding to five different voltages applied, e.g., 0 V, 100 V, 200 V, 300 V and 400 V.

In one embodiment, the optical medium 304 is a liquid crystal cell and each optical state of the liquid crystal cell corresponds to a scattering coefficient (for a certain wavelength) associated with one voltage value applied to the liquid crystal cell. That is, for each voltage value applied to the liquid crystal cell, the liquid crystal cell has a corresponding optical state (or a corresponding scattering coefficient).

Figure 4:
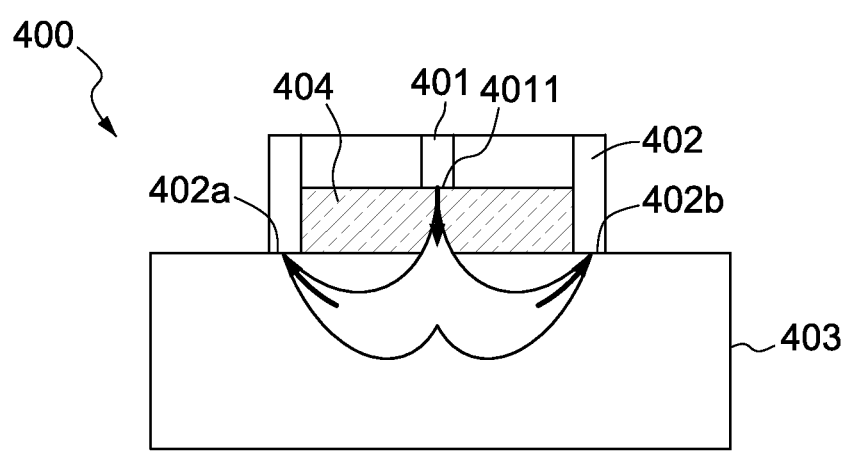
FIG. 4 is a schematic diagram illustrating a DRS device in accordance with one embodiment of the present disclosure.

FIG. 4 is a schematic diagram illustrating an optical device 400 in accordance with one embodiment of the present disclosure. Referring to FIG. 4, the optical device 400 comprises a light emitting unit 401 having a light emitting terminal 4011, a detecting module 402 comprising light receiving terminals 402a, 402b and an optical medium 404. The light emitting terminal 4011 is in contact with a first surface of the optical medium 404. The light receiving terminals 402a and 402b are arranged on the periphery of the optical medium 404.

In one embodiment, the light emitting terminal 4011 is arranged on a central axis of the optical device 400. In one embodiment, the radial distances between the light emitting terminal 4011 and each of the receiving terminals 402a and 402b are substantially equivalent. Accordingly, for the light received at the receiving terminals 402a and 402b, the travelled distances and the penetration depths are substantially equivalent. Therefore, the optical device 400 will not have the drawbacks of a DRS system with multiple source-detector separations, as it only has one source-detector separation.

In one embodiment, the light emitting unit 401 comprises an optical fiber for optically coupling the light emitting terminal 4011 to a steady-state light source (not shown), and the detecting module 402 comprises optical fibers for optically coupling the receiving terminals 402a, 402b to photoelectric sensors and/or spectrometers (not shown). In one embodiment, the optical medium 404 has a thickness of approximately 0.1 mm to 2 mm. In one embodiment, a width or diameter of the optical medium 404 is in a range of about 4 mm to 20 mm (approximately corresponding to the distance between the light receiving terminals 102a and 102b shown in FIG. 4). In one embodiment, the distance between a receiving terminal and the light emitting terminal is about 8 mm.

In one embodiment, the specimen is a biometric tissue. The light scattered by the biometric tissue and received by the receiving terminals may be used to determine the optical property of the biometric tissue, and further to determine the physiological properties, such as oxygen hemoglobin concentration, and the like.

Figure 5:
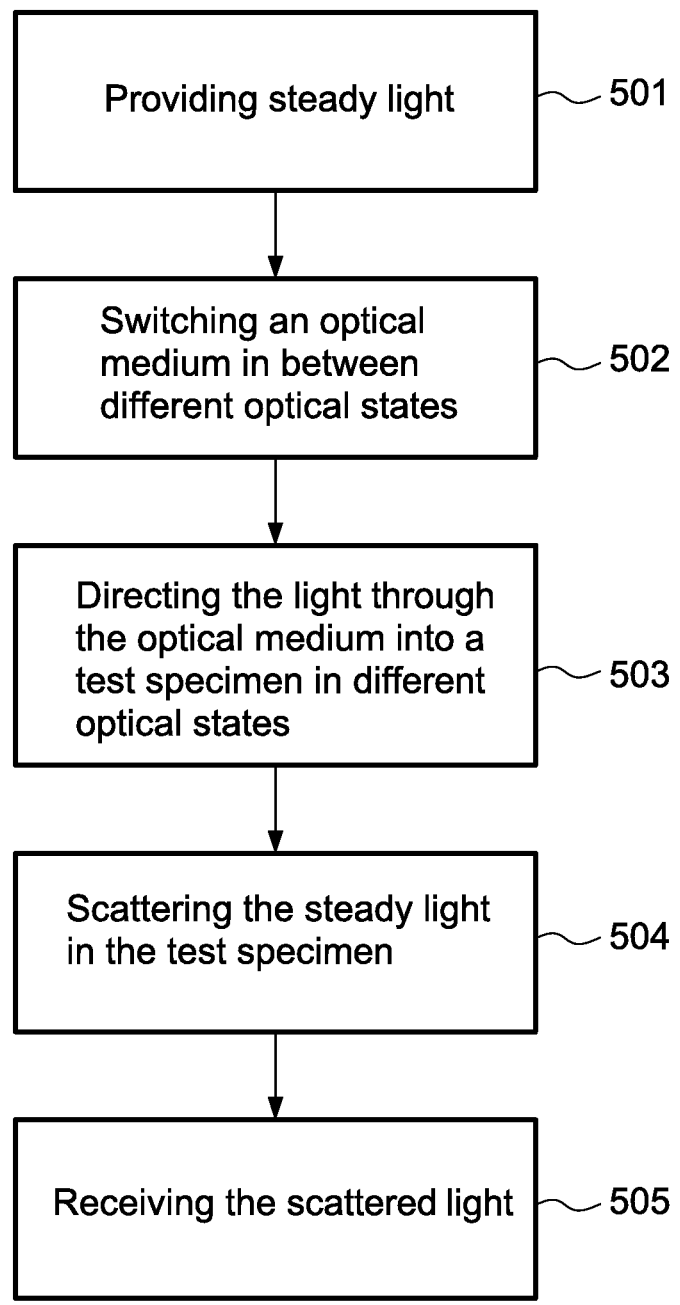
FIG. 5 shows a flowchart schematically illustrating a method of diffuse reflectance spectroscopy in accordance with one embodiment of the present disclosure.

FIG. 5 shows a flowchart schematically illustrating a method for measuring the optical properties of specimen with diffuse reflectance spectroscopy in accordance with one embodiment of the present disclosure. In step 501, a steady-state light (e.g., white light) is provided (by means of a steady-state light source). In step 502, an optical medium having a plurality of different optical states is provided and is controlled to switch between different optical states. In step 503, the steady light is directed through the optical medium into a specimen in different optical states of the optical medium. That is, the steady light may be first directed into a specimen through the optical medium in a first optical state; the optical medium is switched to a second optical state; and the steady light is directed into the specimen through the optical medium in the second optical state. The optical medium may have more than two optical states. In step 504, the steady light is scattered (through the optical medium) into the specimen. In step 505, the light scattered from within the specimen is received and used for determining the optical property of the specimen.

In one embodiment, step 502 further comprises applying different voltages to the optical medium such that the optical medium can switch between different optical states. In one embodiment, the voltages applied to the optical medium range from about 100 V to about 400 V. In one embodiment, switching the optical medium in different optical states comprises changing the absorption coefficients and/or reduced scattering coefficients of the optical medium. In one embodiment, determining the optical property of the specimen comprises calculating a spectrum of the received light scattered from the specimen with a Monte Carlo algorithm and/or a diffusion algorithm. In one embodiment, the optical property comprises at least one of the following: an absorption coefficient and a scattering coefficient. In one embodiment, the specimen is a biometric tissue, wherein the optical property of the biometric tissue is used for determining physiological properties.

The methods and features of this disclosure have been sufficiently described in the above examples and descriptions. It should be understood that any modifications or changes without departing from the spirit of the disclosure are intended to be covered by the scope of the disclosure.

Moreover, the scope of the present application is not intended to be limited to the specific embodiments of the process, machine, manufacture, and composition of matter, means, methods and steps described in the specification. As those skilled in the art will readily appreciate from the disclosure of the present disclosure, processes, machines, manufacture, composition of matter, means, methods or steps presently existing or later to be developed, that perform substantially the same function or achieve substantially the same result as the corresponding embodiments described herein, may be utilized according to the present disclosure. Therefore, the appended claims are intended to include, within their scope, features such as processes, machines, manufacture, compositions of matter, means, methods or steps/operations. Additionally, each claim constitutes a separate embodiment, and the combination of various claims and embodiments are within the scope of the disclosure.

What is claimed:

1. An optical device for determining an optical property of a specimen, comprising:
    a light emitting unit comprising a light emitting terminal, the light emitting unit configured to emit light;
    an optical medium arranged at one end of the device, the optical medium being controllable to switch between multiple optical states and configured to deliver the light to the specimen through the optical medium in different optical states, wherein the optical medium comprises a first surface in contact with the light emitting terminal of the light emitting unit and a second surface for contact with the specimen; and
    a detecting module comprising one or more receiving terminals for receiving light scattered from the specimen for determining the optical property of the specimen.

2. The optical device of claim 1, wherein the optical property comprises at least one of the following: an absorption coefficient and a scattering coefficient.

3. The optical device of claim 1, wherein the optical medium is a turbid medium comprising a liquid crystal, wherein the multiple optical states depend on voltages applied to the turbid medium.

4. The optical device of claim 3, wherein the voltages are in a range from 100 V to 400 V.

5. The optical device of claim 1, wherein each of the one or more receiving terminals comprises a photo sensor.

6. The optical device of claim 1, wherein the one or more receiving terminals are configured to contact the specimen in operation and are arranged on the periphery of the optical medium.

7. The optical device of claim 1, wherein the light emitting terminal is arranged on a central axis of the optical device.

8. The optical device of claim 1, wherein radial distances between the light emitting terminal and each of the one or more receiving terminals are substantially equivalent.

9. The optical device of claim 1, wherein the optical property of the specimen is calculated from the light received at the one or more receiving terminals through a photon transport model.

10. The optical device of claim 1, wherein the specimen is a biometric tissue.

11. The optical device of claim 10, wherein the optical property of the biometric tissue is used for determining physiological properties.

* * * * *